`US007654988B2`

(12) United States Patent
Moulton et al.

(10) Patent No.: US 7,654,988 B2
(45) Date of Patent: Feb. 2, 2010

(54) NEEDLE CAPTURE MECHANISMS

(75) Inventors: William Gary Moulton, Salt Lake City, UT (US); Greg L. Brimhall, West Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/720,240

(22) PCT Filed: Dec. 6, 2005

(86) PCT No.: PCT/US2005/044142

§ 371 (c)(1),
(2), (4) Date: May 1, 2008

(87) PCT Pub. No.: WO2006/062983

PCT Pub. Date: Jun. 15, 2006

(65) Prior Publication Data

US 2009/0012480 A1   Jan. 8, 2009

Related U.S. Application Data

(60) Provisional application No. 60/633,413, filed on Dec. 7, 2004.

(51) Int. Cl.
*A61M 5/00* (2006.01)
(52) U.S. Cl. ...................................................... 604/263
(58) Field of Classification Search .................. 604/110, 604/187, 162–165, 192, 195, 198, 263
See application file for complete search history.

(56) References Cited

FOREIGN PATENT DOCUMENTS

WO   PCT/US2005/044142   12/2005

*Primary Examiner*—Manuel A Mendez
(74) *Attorney, Agent, or Firm*—Mony R. Ghose; Craig Metcalf; Kirton & McConkie (57) ABSTRACT

Needle capture mechanisms and arrangements are provided. One such arrangement includes a needle defining a longitudinal needle axis having a sharp distal tip, a shank portion, and a needle feature defining at least one localized area along the shank of increased outer diameter; a needle shield; and a biasing member adapted to exert a generally downward biasing force upon the needle. Another such arrangement includes a needle defining a longitudinal needle axis having a sharp distal tip, a shank portion, and a needle feature defining at least one localized area along the shank of increased outer diameter; a needle shield, the needle shield comprising a pocket formed therein having an inclined surface; a split collet disposed within the pocket, the split collet having a variable inner bore; and a biasing element disposed within the pocket for biasing the split collet toward the inclined surface of the pocket.

10 Claims, 7 Drawing Sheets

NEEDLE CAPTURE MECHANISMS

This application claims priority to International Application No. PCT/US2005/044142, filed Dec. 6, 2005, which claims priority to U.S. Provisional Application Ser. No. 60/633,413 filed Dec. 7, 2004, both of which are incorporated herein by this reference.

TECHNICAL FIELD

The subject invention relates to mechanisms that will effectively and safely capture a needle or other sharp object, thereby placing the needle or other sharp object in a state that makes accidental contact therewith unlikely or impossible.

BACKGROUND ART

In the following discussion, certain articles and methods will be described for background and introductory purposes. Nothing contained herein is to be construed as an "admission" of prior art. Applicants expressly reserve the right to demonstrate, where appropriate, that the articles and methods referenced herein do not constitute prior art under the applicable statutory provisions.

In recent years, there has been great concern over the contamination of clinicians with a patient's blood and a recognition that blood contaminated sharps must be disposed of to avoid an accidental needle stick. This concern has arisen because of the advent of currently incurable and fatal diseases, such as Acquired Immune Deficiency Syndrome ("AIDS"), which can be transmitted by the exchange of body fluids from an infected person to another person. Thus, contact with the body fluids of an AIDS infected person must be avoided. As noted above, if a needle has been inserted into an AIDS infected person, the needle, via its sharp distal tip, is a vehicle for the transmission of the disease. Although clinicians are aware of the need to properly handle blood contaminated sharps, unfortunately, in certain medical environments such as emergency situations or as a result of inattention or neglect, needle sticks with a blood contaminated sharp still occur.

As a result of the problem of accidental needle sticks by blood contaminated sharps, various needle shields have been developed. Such devices are disclosed in, for example, U.S. Pat. Nos. 5,601,536 and 4,994,041.

Devices such as catheters, catheter introducers and guidewire introducers are all examples of the types of devices that can incorporate a needle or other sharp object therein. Catheters, particularly intravascualar (IV) catheters, are used for infusing fluid, such as normal saline solution, various medicaments and total paternal nutrition, into a patient, withdrawing blood from a patient or monitoring various parameters of the patient's vascular system. Peripheral IV catheters tend to be relatively short and, typically, are on the order of about two inches or less in length. The most common type o IV catheter is an over-the-needle peripheral IV catheter. As its name implies, an over-the-needle catheter is mounted over an introducer needle having a sharp distal tip. At least the distal portion of the catheter tightly engages the outer surface of the needle to prevent peelback of the catheter, thereby facilitating insertion of the catheter into the blood vessel. The catheter and the introducer needle are assembled so that the distal tip of the introducer needle extends beyond the distal tip of the catheter, with the bevel of the needle facing up away from the patient's skin.

The catheter and introducer needle assembly is inserted at a shallow angle through the patient's skin into a blood vessel. There are many techniques for inserting such a catheter and introducer needle assembly into a patient. In one insertion technique, the introducer needle and catheter are inserted completely into the blood vessel together. In another technique, the introducer needle is partially withdrawn into the catheter after the initial insertion into the blood vessel. The catheter is then threaded over the needle and inserted completely into the blood vessel.

To verify proper placement of the catheter in the blood vessel, the clinician confirms that there is flashback of blood in a flashback chamber. The flashback chamber is typically formed as part of the needle hub. Alternatively, where the introducer needle includes a notch, i.e., a hole or opening in the sidewall of the introducer needle, flashback of blood can be observed in the annular space between the introducer needle and the catheter, in the catheter adapter and, where the catheter is an integrated catheter, in an extension tube extending from a side arm formed in the catheter adapter. Once proper placement of the catheter into the blood vessel is confirmed, the clinician applies pressure to the blood vessel by pressing down on the patient's skin over the blood vessel distal to the introducer needle and catheter. This finger pressure occludes, or at least minimizes, further blood flow through the introducer needle and the catheter. The clinician then withdraws the introducer needle, leaving the catheter in place, and attaches an appropriate device to the catheter. Such a device can include a fluid delivery device, a PRN, a deadender cap or a blood pressure monitoring probe. Once the introducer needle is withdrawn from the catheter, the introducer needle is a blood contaminated sharp and must be properly handled.

It would be desirable, in general, to provide a needle capture and shielding arrangement having an improved capture mechanism. For instance, some conventional needle capture mechanisms can require a relatively large amount of space within the apparatus into which it is incorporated. Moreover, some conventional needle capture mechanisms require the user to undertake specific steps or actions to activate the capture mechanism; such steps or measures are often not intuitive. Thus there is a need to provide relatively compact needle capture mechanisms that are easy to use.

DISCLOSURE OF THE INVENTION

Therefore, according to certain embodiments, the present invention comprises a device or method that provides one or more of the following features and advantages: a needle capture device and arrangement that is compact, simple and easy to use, requires no special features or techniques to be operative, and has a relatively low cost.

According to one aspect of the present invention, there is provided an arrangement comprising: a needle defining a longitudinal needle axis having a sharp distal tip, a shank portion, and a needle feature defining at least one localized area along the shank of increased outer diameter; a needle shield defining a longitudinal central axis, the needle shield comprising a proximal opening having a diameter great enough to permit passage of the needle shank therethrough, but small enough to prevent the needle feature from passing therethrough, a distal opening having a diameter great enough to allow both the needle shank and needle feature to pass therethrough, and an inner shoulder surface; and a biasing member adapted to exert a generally downward biasing force upon the needle; wherein the arrangement is constructed such that upon drawing the needle completely through the distal needle passage, the downward biasing force of the biasing element causes the needle to become angled downwardly such that the central axis and the needle axis diverge, and the sharp tip of the needle is forced out of registry with the distal needle passage and is trapped within the needle shield by the inner shoulder surface.

According to the invention, the above-described arrangement further comprises: a catheter adapter having a proximal end; a catheter mounted within the catheter adapter; and an external coupling housing comprising a proximal end, the external coupling housing being received within the proximal end of the catheter adapter; and wherein the needle shield is received within the proximal end of the catheter adapter.

According to another aspect of the present invention, the above-described needle shield is retained within the external coupling housing by one or more of the following: a folded tab, one or more areas of increased outer diameter along the external periphery of the needle shield, an adhesive, a frangible link and a mechanical fastener.

According to the invention, the above-described biasing member comprises one or more of: a finger spring in the form of a folded tab cut from the sidewall of the needle shield; a mechanical spring; an elastomeric spring; a pneumatic element; and an electromechanical element.

According to the invention, the above-described catheter adapter and external coupling housing are formed from a thermoplastic material, such as a polyamide, a polytetrafluoroethylene, a fluorinated ethylene propylene, a polyurethane, or a metallic material.

According to the invention, the above-described needle feature comprises a crimp or a ferrule.

According to the invention, the above-described arrangement is constructed such that the needle shield, having a needle captured therein is separable from one or more of the catheter adapter and the external coupling housing.

According to another aspect, the present invention provides an arrangement comprising: a needle defining a longitudinal needle axis having a sharp distal tip, a shank portion, and a needle feature defining at least one localized area along the shank of increased outer diameter; a needle shield defining a longitudinal central axis, a proximal through-hole opening and a distal through-hole opening, the needle shield comprising a pocket formed therein having an inclined surface; a split collet disposed within the pocket, the split collet having a variable inner bore; and a biasing element disposed within the pocket for biasing the split collet toward the inclined surface of the pocket; wherein the arrangement is constructed such that as the needle is drawn in toward the interior of the needle shield, the needle feature comes into contact with the split collet, which causes compression of the biasing element such that the split collet no longer contacts the inclined pocket surface and the inner bore of the split collet is expanded, thereby allowing passage of the needle feature through the split collet with a predetermined degree of interference therewith, and further as the sharp distal tip of the needle is completely withdrawn into the needle shield housing, the needle feature passes out of the inner bore of the split collet, thereby removing the aforementioned compression of the biasing element, which causes the split collet to once again be biased against the inclined surface, this also causes the inner bore of the split collet to constrict such that it is once again smaller in diameter than the distal through-hole opening, as well as the outer diameter of the needle feature, thereby preventing the sharp distal tip of the needle from exiting the needle shield housing.

According to the invention, the above-described needle shield and/or split collet is formed from a thermoplastic material, such as a polyamide, a polytetrafluoroethylene, a fluorinated ethylene propylene, a polyurethane, or a metallic material.

According to the invention, the above-described needle feature comprises a crimp or a ferrule.

According to the invention, the above-described biasing element comprises one or more of: a mechanical spring, a metal or plastic clip, an elastomeric element, or magnetic force.

According to the invention, the above-described split collet is in the form of an annular ring comprising a plurality of arcuate segments having interfitting end configurations.

According to the invention, the above-described split collet is in the form of a split one-piece annular ring comprising interfitting end configurations.

According to the invention, the above described wherein the split collet comprises a distal lead-in chamfered surface.

According to the invention, the above-described split collet comprises an inner bore and a radially extending surface.

According to the invention, the above-described arrangement further comprises: a catheter adapter having a proximal end; a catheter mounted within the catheter adapter; and an external coupling housing comprising a proximal end, the external coupling housing being received within the proximal end of the catheter adapter; and wherein the needle shield is received within the proximal end of the catheter adapter.

According to a further aspect of the invention, there is provided a method of making a needle safe, the needle comprising a longitudinal axis comprising a sharp distal tip, a shank portion, and a needle feature defining at least one localized area along the shank of increased outer diameter, the method comprising: providing a needle shield defining a longitudinal central axis and comprising a proximal opening having a diameter great enough to permit passage of the needle shank therethrough, but small enough to prevent the needle feature from passing therethrough, and a distal opening having a diameter great enough to allow both the needle shank and needle feature to pass therethrough, and an inner shoulder surface; providing a biasing member adapted to exert a generally downward biasing force upon the needle; drawing the needle completely through the distal needle passage; applying a downward biasing force on the needle with the biasing member causing the needle to become angled downwardly such that the central axis and the needle axis diverge, and forcing the sharp tip of the needle out of registry with the distal needle passage thereby trapping the needle within the needle shield by the inner shoulder surface.

According to yet another aspect of the invention, there is provided a method of making a needle safe, the needle comprising a longitudinal axis comprising a sharp distal tip, a shank portion, and a needle feature defining at least one localized area along the shank of increased outer diameter, the method comprising: providing a needle shield defining a longitudinal central axis, a proximal through-hole opening and a distal through-hole opening, and comprising a pocket formed therein comprising an inclined surface; locating a split collet within the pocket having a variable inner bore; and disposing a biasing element within the pocket for biasing the split collet toward the inclined surface of the pocket; drawing the needle toward the interior of the needle shield such that the needle feature comes into contact with the split collet; compressing the biasing element such that the split collet no longer contacts the inclined pocket surface and the inner bore of the split collet is expanded, thereby allowing passage of the needle feature through the split collet with a predetermined degree of interference therewith; further drawing the needle such that the needle feature passes out of the inner bore of the split collet thereby removing the aforementioned compression of the biasing element, which causes the split collet to once again be biased against the inclined surface, and also causing the inner bore of the split collet to constrict such that it is once again smaller in diameter than the distal through-hole opening as well as the outer diameter of the needle feature, thereby preventing the sharp distal tip of the needle from exiting the needle shield housing.

BRIEF DESCRIPTION OF THE DRAWINGS

The preferred embodiments are illustrated in the drawings in which like reference numerals refer to the like elements.

MODES FOR CARRYING OUT THE INVENTION

The principles of the present invention will now be further described by the following discussion of certain illustrative embodiments thereof and by reference to the foregoing drawing figures.

As used herein, the term "proximal" refers to a location on the catheter and introducer needle assembly with needle shield of this invention that, during normal use, is closest to the clinician using the device and farthest from the patient in connection with whom the device is used. Conversely, the term "distal" refers to a location on the catheter and introducer needle assembly of this invention that, during normal use, is farthest from the clinician using the device and closest to the patient in connection with whom the device is used.

As used herein, the term "top," "up" or "upwardly" refers to a location on the catheter and introducer needle assembly with needle shield of this invention that, during normal use, is radially away from the longitudinal axis of the device and away from the patient's skin. Conversely, as used herein, the term "bottom," "down" or "downwardly" refers to a location on the catheter and introducer needle assembly of this invention that, during normal use, is radially away from the longitudinal axis of the device and toward the patient's skin.

As used herein, the term "in" or "inwardly" refers to a location with respect to the catheter and introducer needle assembly with needle shield of this invention that, during normal use, is toward the inside of the device. Conversely, as used herein, the term "out" or "outwardly" refers to a location with respect to the catheter and introducer needle assembly of this invention that, during normal use, is toward the outside of the device.

As used herein, the term "needle" refers to a member having at least one relatively sharp end. The member may be either hollow or solid in cross-section. The member may have any number of suitable dimensions and/or geometries.

The present invention is described herein using the same reference numbers for like elements in the different embodiments. Although this invention is described herein in connection with various devices and assemblies, it is to be understood that this invention is usable alone and is also applicable to other devices. For example, this invention is applicable to standard IV catheters and extended dwell catheters requiring the needle to be connected to the needle hub by a stylet, as well as other medical devices where it is desirable for a needle to be shielded after use such as anesthesia needles, epidural needles, catheter introducers and hypodermic syringes.

Figure 1:
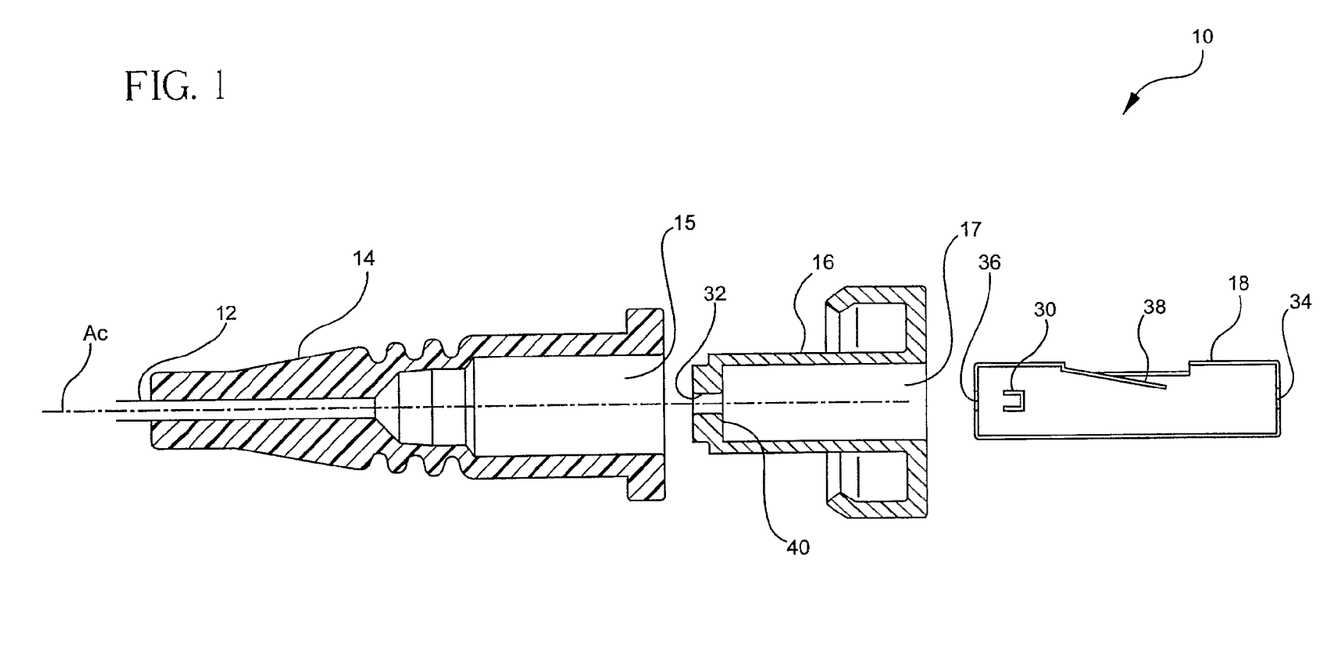
FIG. 1 is a cross-sectional exploded view of an assembly constructed according to the principles of a first embodiment of the present invention.
Figure 2:
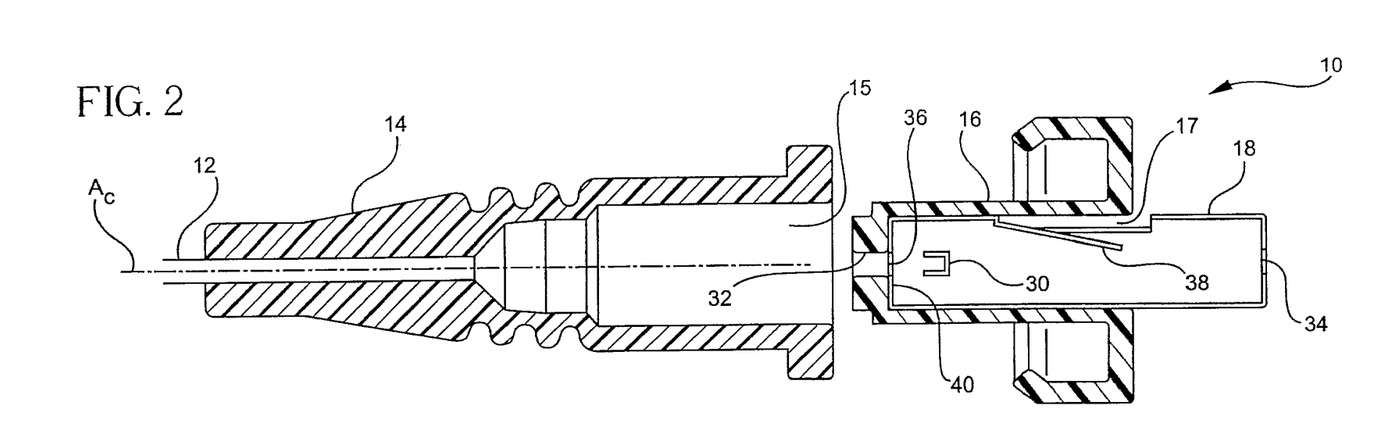
FIG. 2 is cross-sectional view of the assembly of FIG. 1, shown in a partially-assembled state.
Figure 3:
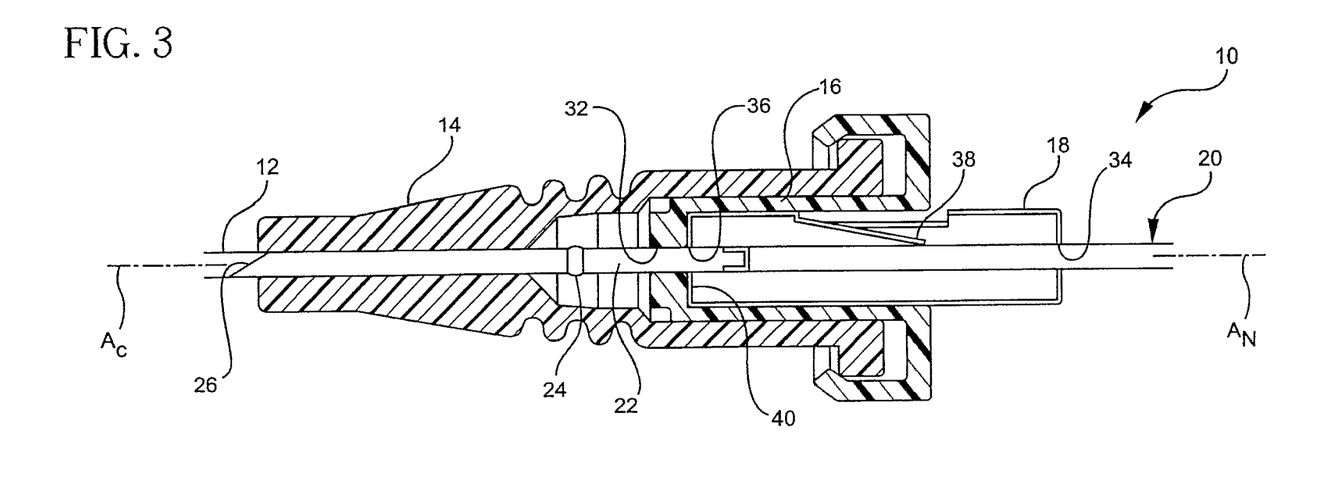
FIG. 3 is a cross-sectional view of the arrangement of FIG. 1, shown in a fully assembled condition and with a needle located in a first position.

A first illustrative embodiment of the present invention is depicted in FIGS. 1-5. As best illustrated in FIGS. 1-3, this embodiment can be identified generally as an over-the-needle catheter assembly 10. The assembly 10 defines a central longitudinal axis AC. The catheter assembly 10 includes a catheter 12 mounted within a catheter adapter 14. The proximal end 15 of the catheter adapter 14 receives an external coupling housing member 16 therein.

A needle shield 18 is also included in the catheter assembly 10. The needle shield 18 is received within the proximal end 17 of the external coupling housing 16. The needle shield 18 is optionally provided with a retention means 30, which acts to secure the needle shield 18 within the external coupling housing 16. According to the illustrated embodiment, the retention means 30 is in the form of a folded tab cut out of a sidewall of the needle shield 18. It is within the scope of the present invention that alternative constructions for retaining the needle shield 18 are encompassed within the scope of the present invention. For example, the needle shield 18 may be provided with one or more areas of increased outer diameter along the periphery thereof (not shown), which would also act to secure the needle shield 18 within the external coupling housing 16. Moreover, various adhesives and/or mechanical fasteners and/or frangible links may be utilized as the retention means to accomplish the same functionality.

As illustrated, for example, in FIG. 3, the assembly 10 further includes a needle 20 concentrically disposed within the catheter 12. The needle 20 defines a longitudinal axis AN extending therethrough.

According to the illustrated embodiment, the needle 20 comprises a shank 22 having a needle feature 24 provided thereon. The needle feature 24 provides the shank 22, on at least a portion thereof, with a localized area of increased outer diameter. In this regard, numerous physical constructions for providing this area of increased outer diameter are envisioned. For example, the needle feature 24 may comprise a crimp in the shank 22 of the needle 20, thereby defining a localized area of increased outer diameter, relative to adjacent sections of the needle shank 22. Alternatively, the needle feature 24 may comprise a ferrule. The ferrule can comprise either a separate member fixably attached to the shank 22 or an integral portion of increased diameter such that the shank and ferrule comprise a one-piece monolithic part. The term "ferrule" as utilized herein is intended to encompass each of the above-described alternative constructions.

The above-described components of the assembly 10 can be formed from any suitable material or combinations of different materials. For example, the catheter adapter 14 and the external coupling housing 16 can be made of similar or different thermoplastic materials. Suitable materials include polyamide, polytetrafluoroethylene, fluorinated ethylene propylene, polyurethane and the like. The needle shield 18 can also be formed of any suitable material, such as a metallic material or any of the above-described thermoplastic materials The assembly 10 further comprises a biasing member for exerting a biasing force on the needle 20. When constructed of a metallic material, it is convenient that the needle shield 18 be provided with an integral biasing member 38. According to the illustrated embodiment, the biasing member 38 includes a finger-spring element, which is formed by cutting and folding the side-wall of the needle shield 18. It should be understood, however, that many different biasing elements are envisioned by the present invention. Any suitable mechanical spring member could be substituted. Alternatively, a metal or plastic clip, elastomeric and/or magnetic biasing elements are possible.

Operation of the illustrated embodiment of the present invention will now be described by reference to FIGS. 3-5. As illustrated in FIG. 3, the shank 22 of the needle 20 is disposed within the catheter 12, extends therethrough and passes through the coupling housing needle passage 32. The shank 22 continues and extends to both the proximal and distal openings 34 and 36, respectively, of the needle shield 18 (see, e.g., FIG. 1). As the needle 20 extends through the needle shield 18, the biasing element 38 is in contact with the shank 22 and exerts a generally downward biasing force thereon. In the state illustrated in FIG. 3, it is evident that the central axis AC and the longitudinal axis of the needle AN substantially coincide.

Figure 4:
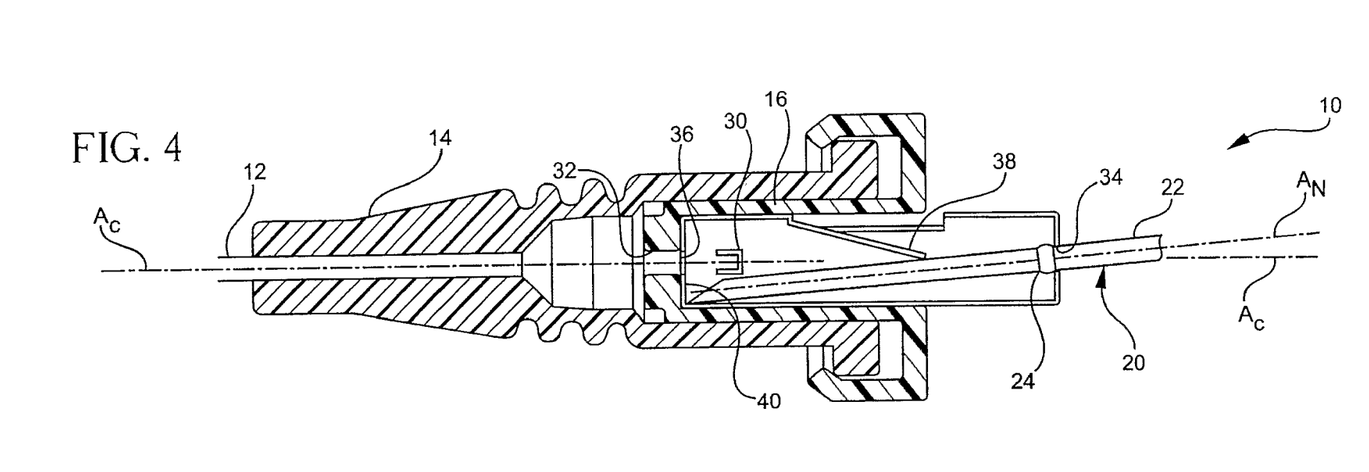
FIG. 4 is a cross-sectional view of the arrangement of FIG. 3, wherein the needle is shown in a second, withdrawn position.

As illustrated in FIG. 4, as the needle 20 is withdrawn in the proximal direction, the shank 22 is withdrawn from the catheter 12 and eventually passes completely through the coupling housing needle passage 32, as well as the distal needle passage 36 of the needle shield 18. In this state, the sharp tip 26 of the needle 20 is located entirely within the confines of the needle shield 18. Once the needle 20 has been completely withdrawn through the coupling housing needle passage 32 and the distal needle passage 36, the downward biasing force of the biasing element 38 causes the needle to become angled downwardly such that the central axis AC and the needle axis AN diverge and no longer coincide. As illustrated in FIG. 4, the sharp tip 26 of the needle 20 is forced out of registry with the distal needle passage 36 and the coupling housing needle passage 32 by the downward force of the biasing element 38. The sharp tip 26 of the needle 20 is trapped within the needle shield 18 by inner shoulder surface 40 thereby preventing unwanted movement of the needle 20 in the distal direction. Moreover, unwanted movement of the needle 20 in the proximal direction is also prevented by virtue of the fact that the needle feature 24, having at least a localized area of increased outer diameter, prevents further passage of the needle shank 22 through the proximal needle passage 34 of the needle shield 18. In other words, the inner diameter of the proximal needle passage 34 is smaller then the outer diameter of the needle feature 24. Thus, it is evident that the needle 20 has been made safe within the needle shield 18.

Figure 5:
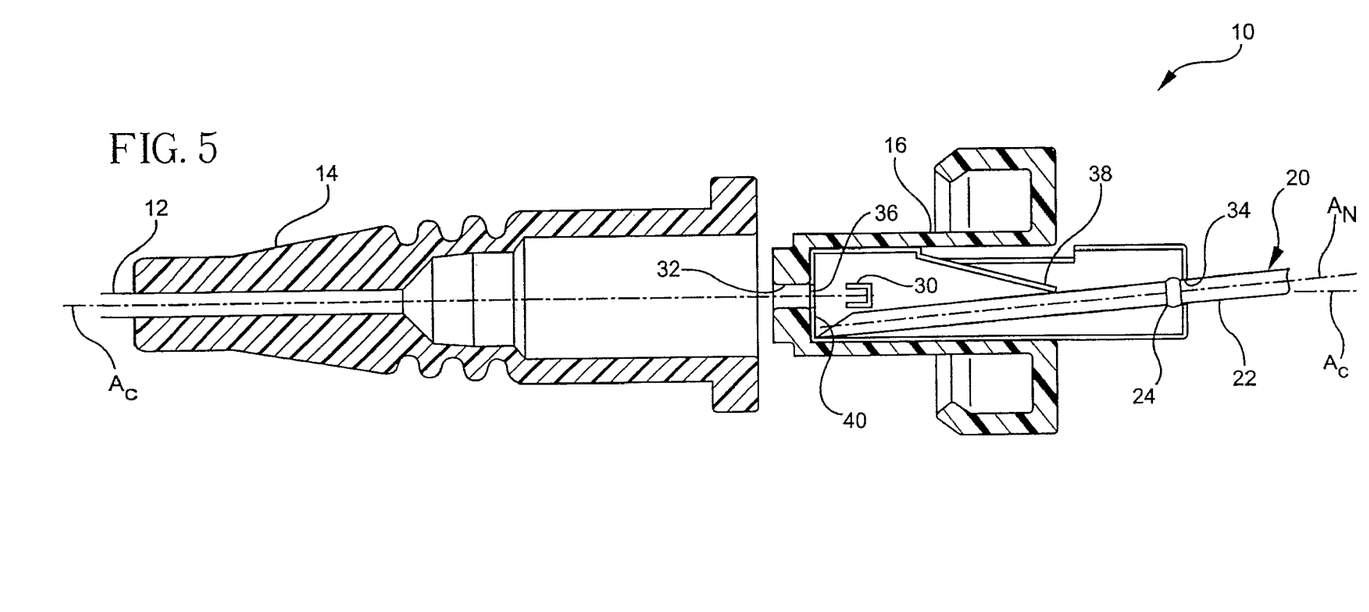
FIG. 5 is a cross-sectional view of the arrangement of FIG. 4, wherein the arrangement is in a partially disassembled condition.

As illustrated in FIG. 5, the external coupling housing 16, with the needle shield 18 and captured needle 20 contained therein, can be jointly removed from the catheter adapter 14 for safe and convenient disposal. Alternatively, the needle shield 18 may be separable from the external coupling housing.

While the principles of this embodiment of the present invention have been described by reference to a specific illustrated embodiment, it should be understood that the scope of this embodiment of the present invention is not confined thereto. Namely, the needle capture mechanism of this embodiment of the present invention can be generally described as follows. A needle shield is constructed to permit a needle to be at least partially drawn therethrough. When the sharp tip of the needle has been drawn completely within the confines of the needle shield, a downwardly acting biasing force acts to push the needle in a direction that causes a change in the angular orientation of its longitudinal axis. This change in the angular orientation of the longitudinal axis of the needle, coupled with the physical construction of the needle shield, prevents the sharp tip of the needle from exiting one end of the needle shield. In addition, the needle is provided with a feature that, in conjunction with the construction of the needle shield, prevents further undesired movement of the needle out of the opposing end of the needle shield.

A second embodiment of a needle capture mechanism and arrangement formed according to the principles of the present invention is depicted in FIGS. 6-9. As illustrated, for example, in FIG. 6, a needle shield arrangement 100 comprises a needle shield housing 102 having a proximal through-hole opening 104, a distal through-hole opening 106, and defining a longitudinal central axis AC. A needle shield housing 102 is formed with a pocket 108 that is defined, at least in part, by an inclined surface 110, a radially-extending pocket surface 112, and an interconnecting longitudinal surface 114. The needle shield housing 102 can be formed from any suitable material, such as a metal or a thermoplastic material of the type identified in the description of the first embodiment.

Figure 6:
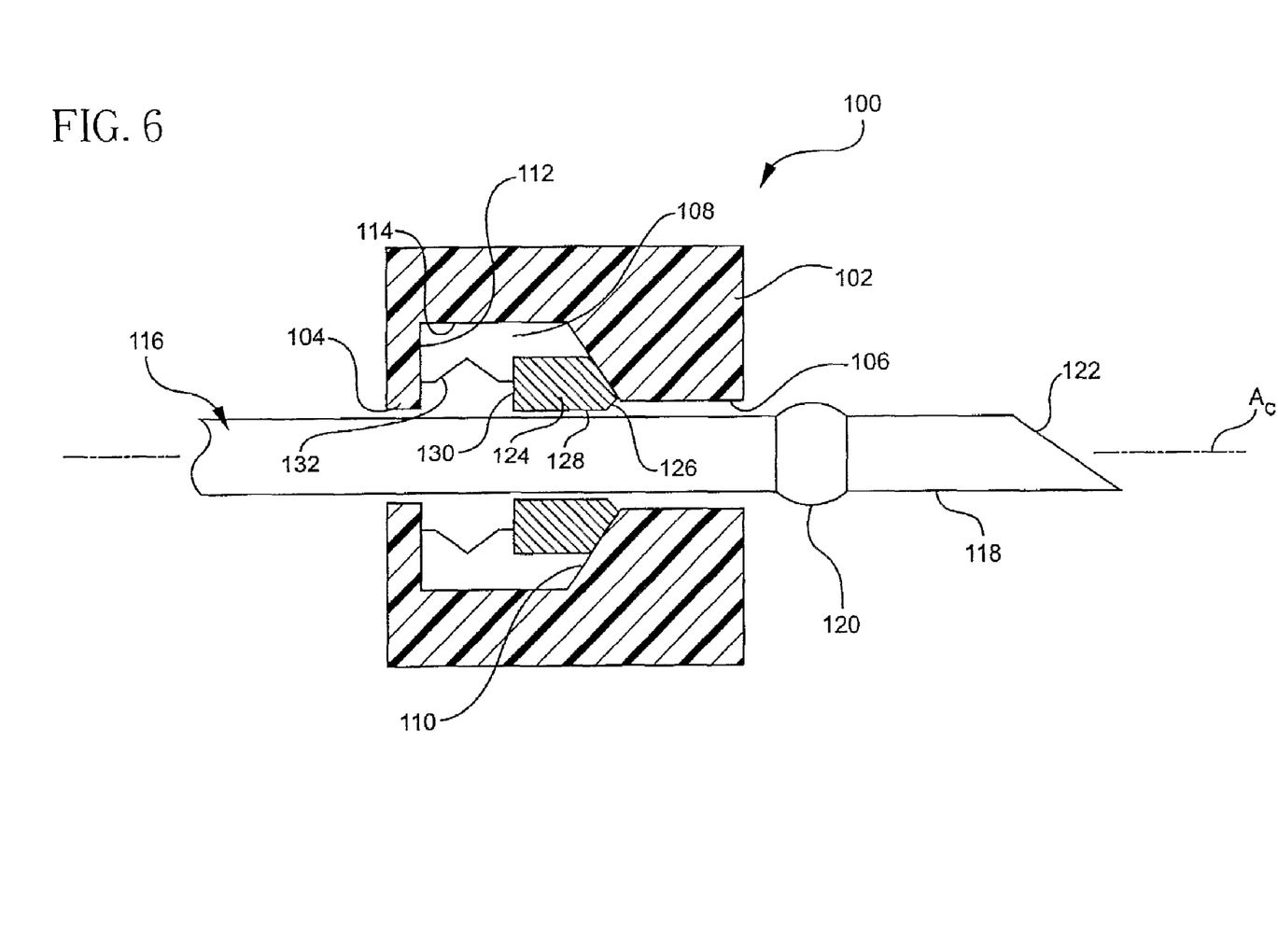
FIG. 6 is a cross-sectional view of a second embodiment of a needle capture mechanism and arrangement formed according to the principles of the present invention, in a first position or state.

A needle 116 is received through the proximal through-hole opening 104, as well as the distal through-hole opening 106. The needle 116 comprises a shank portion 118, as well as a needle feature 120 disposed thereon. The needle feature 120 provides at least a localized area of increased outer diameter. Numerous constructions are envisioned as being capable of providing this feature. For example, the needle feature 120 may comprise a crimp in the wall of the needle, thereby providing a localized area of increased outer diameter. Alternatively, the needle feature 120 may comprise a ferrule. As used herein, the term "ferrule" refers to a separate member fixably attached to the shank portion 118 of the needle 116, thereby providing at least a localized area of increased outer diameter. In addition, the term "ferrule" is intended to encompass a construction wherein the ferrule comprises an integral part of the shank 118, thereby defining a one-piece monolithic construction composed of both the needle feature 120 and the shank portion 118. The needle 116 further comprises a sharp distal tip 122.

The assembly 100 further comprises a split collet 124 disposed within the pocket 108 of the needle shield housing 102. The split collet 124 is generally in the form of an annular ring member. According to the illustrated embodiment, the split collet 124 comprises a distal lead-in chamfered surface 126, an inner bore 128, and a proximal radially-extending surface 130. The split collet can be formed from any suitable material, such as a metal or a thermoplastic of the type identified in connection with the description of the first embodiment.

A biasing element 132 is also located within the pocket 108 and is disposed generally between the proximal pocket surface 112 and the proximal radially-extending surface 130 of the split collet 124. The biasing element 132 can comprise many different types of elements. According to the illustrated embodiment, the biasing element 132 is schematically illustrated as a mechanical spring member. Further constructions are comprehended. For example, the biasing element 132 may comprise a metal or plastic clip, an elastomeric element or a magnetic element.

Figure 7A:
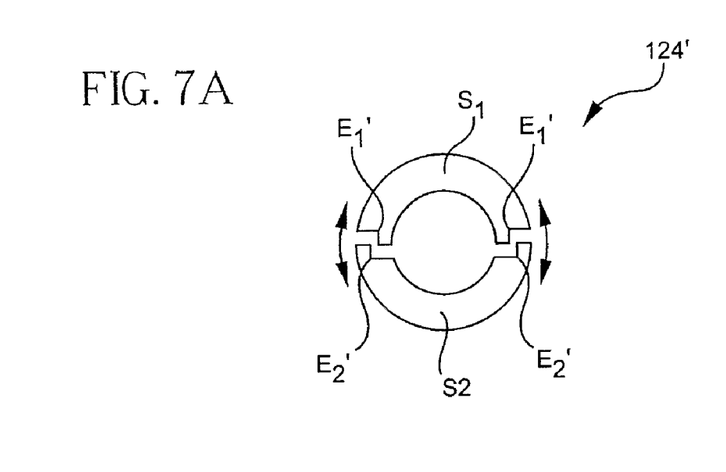
FIG. 7A is a top view of one of the components of the arrangements of FIG. 6 formed according to a first alternative construction.
Figure 7B:
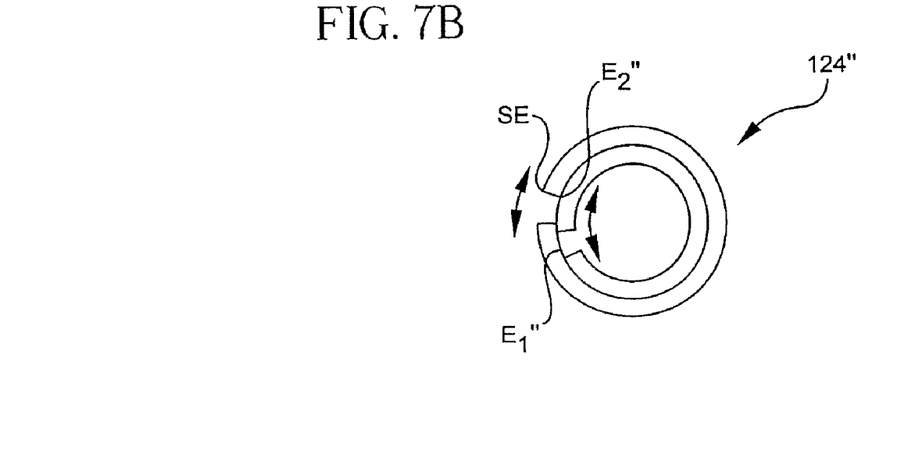
FIG. 7B is a top view of a component of the arrangement of FIG. 6 having a second alternative construction.

As noted above, the collet 124 has a split annular configuration. This split annular configuration allows for a predetermined degree of expansion and contraction of the inner diameter, as defined by the inner bore 128. As illustrated in FIGS. 7A-7B, the split collet 124 can be in the form of a single piece ring or multiple arcuate segments.

FIG. 7A is illustrative of a split collet 124' in the form of a plurality of arcuate segments S1 and S2. While this embodiment of the split collet 124' is shown as comprising two arcuate segments, it should be understood that it is possible to construct the split collet from three or more such arcuate segments. As further illustrated in FIG. 7A, each of the arcuate segments S1, S2 has interfitting ends E'1 and E'2, respectively, which permit the aforementioned expansion and contraction of the inner diameter of the split collet 124. In the illustrated embodiment, these interfitting ends E'1 and E'2 are in the form of a staircase-type geometry. It is envisioned, however, that numerous other geometries may be provided to the interfitting ends, so long as the desired expansion and contraction of the inner diameter of the split collet 124 can be accommodated.

FIG. 7B is illustrative of an alternative construction of the split collet which comprises a single piece split ring 124". The one-piece ring 124" has a split end configuration SE. According to the illustrated example, the split end SE has a first and second mating end configuration E"1 and E"2. Once again, the end constructions E"1 and E"2 are shown in the form of a staircase-type geometry, which permits the desired expansion and contraction of the inner diameter of the split collet 124". As noted above, however, numerous other geometrical configurations are contemplated, so long as they accommodate the desired expansion and contraction of the inner diameter of the split collet 124".

The operation of this embodiment of the present invention will now be described by reference to drawings FIGS. 6, 8 and 9. As illustrated in FIG. 6, in a state in which the sharp distal tip 122 of the needle 116 is disposed entirely outside of the needle shield housing 102, the split collet 124 is urged in a forward, or distal, direction under the action of the biasing element 132. As the split collet 124 is forced against the inclined surface 110 under the action of the biasing element 132, the split collet 124 is radially compressed; thereby reducing the inner diameter as defined by the inner bore 128. As illustrated in FIG. 6, in this state, the inner bore 128 defines a diameter smaller than the distal through-hole opening 106, and is smaller than the outer diameter of the needle feature 120.

Figure 8:
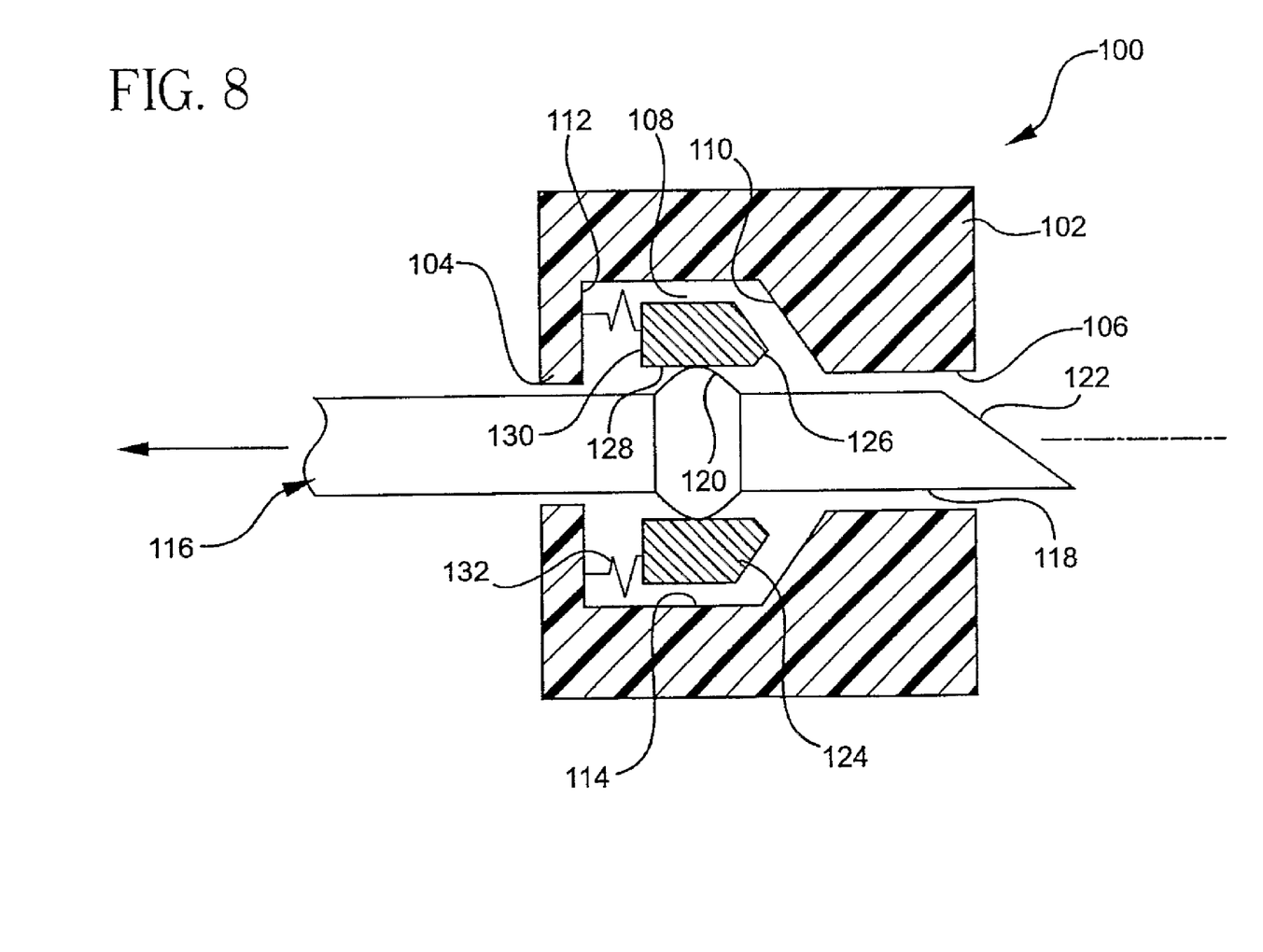
FIG. 8 is a cross-sectional view of the arrangement of FIG. 6 shown in a second position or state.

FIG. 8 illustrates the arrangement 100 in a state in which the needle 116 has been partially drawn into the needle shield housing 102 in the proximal direction. As the needle 116 is withdrawn in the proximal direction, the needle feature 120 comes into contact with the chamfered lead-in surface 126 of the split collet 124. This contact causes compression of the biasing element 132 such that the split collet no longer contacts the inclined pocket surface 110. In the state illustrated in FIG. 8, the inner diameter of the split collet 124, as defined by the inner bore 128, is permitted to expand. This allows for passage of the needle feature 120 through the inner bore 128 with a degree of interference therewith.

Figure 9:
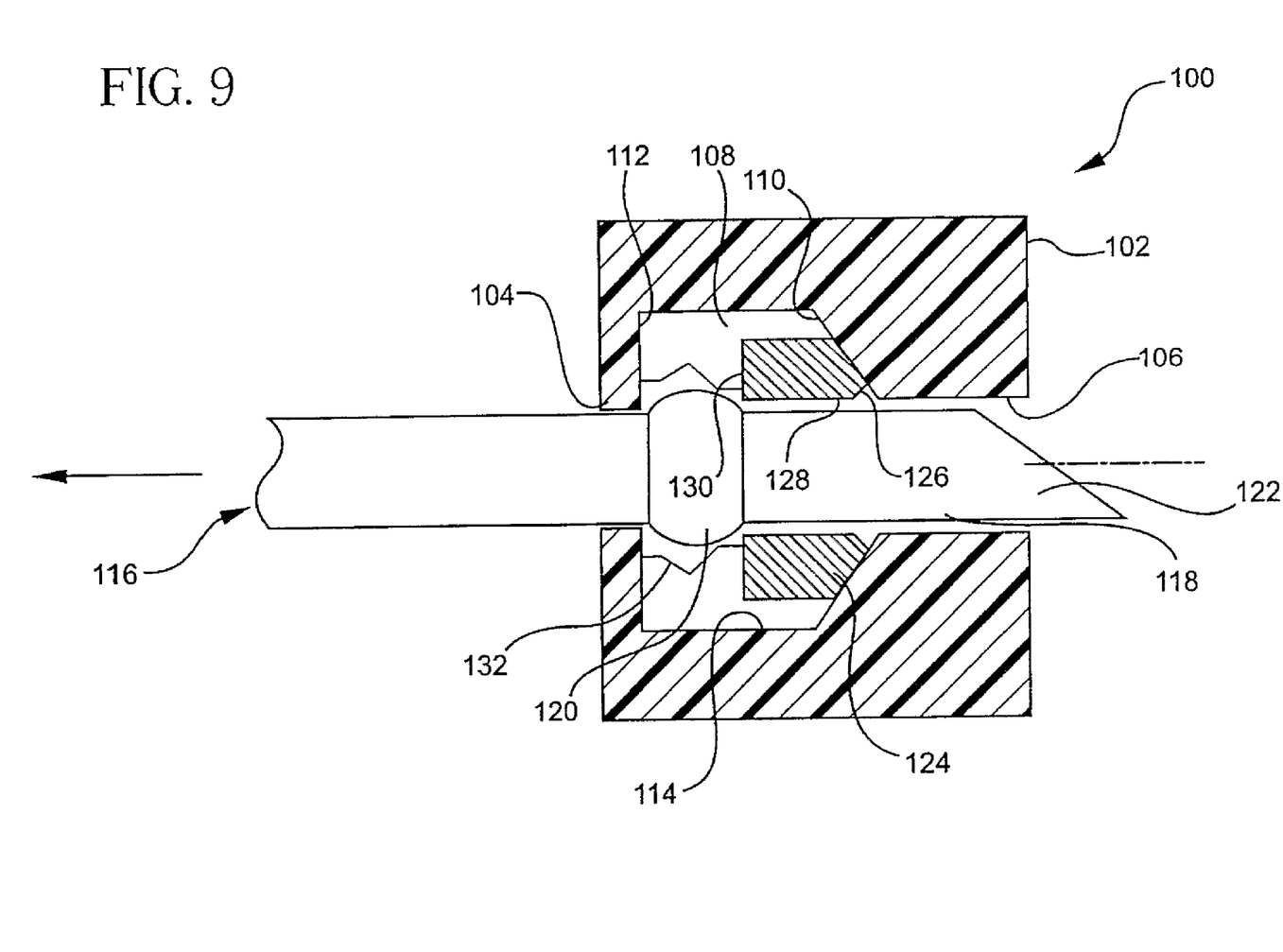
FIG. 9 is a cross-sectional view of the arrangement of FIG. 6 shown in a third position or state.

As illustrated in FIG. 9, as the sharp distal tip 122 of the needle 116 is completely withdrawn into the needle shield housing 102, the needle feature 120 passes out of the inner bore 128 of the split collet 124, thereby removing the aforementioned compression of the biasing element 132, which causes the split collet 124 to be once again urged against the inclined pocket surface 110, thereby contracting the inner diameter as defined by the inner bore 128. The inner bore 128 is once again smaller in diameter than the outer diameter of the needle feature 120. In addition, the diameter defined by the bore of the proximal through-hole opening 104 is smaller than the outer diameter of the needle feature 120. Given these relative dimensions, it is evident that the needle feature 120 is trapped between the proximal pocket surface 112 and the proximal radially extending surface 130. Thus, the needle 116 trapped in a positioned such that the sharp distal tip 122 is located within the needle shield housing 102.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents.

We claim:

1. An arrangement comprising:
   a needle defining a longitudinal needle axis having a sharp distal tip, a shank portion, and a needle feature defining at least one localized area along the shank of increased outer diameter;
   a needle shield defining a longitudinal central axis, a proximal through-hole opening and a distal through-hole opening, the needle shield comprising a pocket formed therein comprising an inclined surface;
   a split collet disposed within the pocket, the split collet having a variable inner bore; and
   a biasing element disposed within the pocket for biasing the split collet toward the inclined surface of the pocket;
   wherein the arrangement is constructed such that as the needle is drawn in toward the interior of the needle shield, the needle feature comes into contact with the split collet, which causes compression of the biasing element such that the split collet no longer contacts the inclined pocket surface and the inner bore of the split collet is expanded, thereby allowing passage of the needle feature through the split collet with a predetermined degree of interference therewith, and further as the sharp distal tip of the needle is completely withdrawn into the needle shield housing, the needle feature passes out of the inner bore of the split collet thereby removing the aforementioned compression of the biasing element, which causes the split collet to once again be biased against the inclined surface, and also causing the inner bore of the split collet to constrict such that it is once again smaller in diameter than the distal through-hole opening as well as the outer diameter of the needle feature, thereby preventing the sharp distal tip of the needle from exiting the needle shield housing.

2. The arrangement of claim 1, wherein at least one of the needle shield and split collet is formed from a polyamide, a polytetrafluoroethylene, a fluorinated ethylene propylene, a polyurethane, or a metallic material.

3. The arrangement of claim 1, wherein the needle feature comprises a crimp or a ferrule.

4. The arrangement of claim 1, wherein the biasing element comprises one or more of: a mechanical spring, a metal or plastic clip, an elastomeric element, or magnetic force.

5. The arrangement of claim 1, wherein the split collet is in the form of an annular ring comprising a plurality of arcuate segments having interfitting end configurations.

6. The arrangement of claim 1, wherein the split collet is in the form of a split one-piece annular ring comprising interfitting end configurations.

7. The arrangement of claim 1, wherein the split collet comprises a distal lead-in chamfered surface.

8. The arrangement of claim 1, wherein the split collet comprises an inner bore and a radially extending surface.

9. The arrangement of claim 1, further comprising:
   a catheter adapter comprising a proximal end;
   a catheter mounted within the catheter adapter; and
   an external coupling housing comprising a proximal end, the external coupling housing being received within the proximal end of the catheter adapter;
   wherein the needle shield is received within the proximal end of the catheter adapter.

10. A method of making a needle safe, the needle comprising a longitudinal axis comprising a sharp distal tip, a shank portion, and a needle feature defining at least one localized area along the shank of increased outer diameter, the method comprising:

providing a needle shield defining a longitudinal central axis, a proximal through-hole opening and a distal through-hole opening, and comprising a pocket formed therein comprising an inclined surface;

locating a split collet within the pocket having a variable inner bore; and disposing a biasing element within the pocket for biasing the split collet toward the inclined surface of the pocket;

drawing the needle toward the interior of the needle shield such that the needle feature comes into contact with the split collet;

compressing the biasing element such that the split collet no longer contacts the inclined pocket surface and the inner bore of the split collet is expanded, thereby allowing passage of the needle feature through the split collet with a predetermined degree of interference therewith;

further drawing the needle such that the needle feature passes out of the inner bore of the split collet thereby removing the aforementioned compression of the biasing element, which causes the split collet to once again be biased against the inclined surface, and also causing the inner bore of the split collet to constrict such that it is once again smaller in diameter than the distal through-hole opening as well as the outer diameter of the needle feature, thereby preventing the sharp distal tip of the needle from exiting the needle shield housing.

* * * * *